(12) United States Patent
Chen et al.

(10) Patent No.: US 9,504,475 B2
(45) Date of Patent: Nov. 29, 2016

(54) DELIVERY WIRE FOR OCCLUSIVE DEVICE DELIVERY SYSTEM

(71) Applicants: STRYKER CORPORATION, Kalamazoo, MI (US); STRYKER NV OPERATIONS LIMITED, Dublin (IE)

(72) Inventors: Hancun Chen, Fremont, CA (US); Jimmy Dao, San Jose, CA (US); Richard Murphy, Sunnyvale, CA (US)

(73) Assignees: Stryker Corporation, Kalamazoo, MI (US); Stryker European Holdings I, LLC, Kalamazoo, MI (US)

( * ) Notice: Subject to any disclaimer, the term of this patent is extended or adjusted under 35 U.S.C. 154(b) by 458 days.

(21) Appl. No.: 14/281,245

(22) Filed: May 19, 2014

(65) Prior Publication Data

US 2014/0249570 A1 Sep. 4, 2014

Related U.S. Application Data

(63) Continuation of application No. 12/752,914, filed on Apr. 1, 2010, now abandoned.

(60) Provisional application No. 61/166,888, filed on Apr. 6, 2009.

(51) Int. Cl.
  *A61M 29/00* (2006.01)
  *A61B 17/12* (2006.01)
  *A61M 25/09* (2006.01)

(52) U.S. Cl.
  CPC ..... *A61B 17/12113* (2013.01); *A61B 17/1214* (2013.01); *A61B 17/1215* (2013.01);
  (Continued)

(58) Field of Classification Search
  CPC .................. A61B 17/12109; A61B 17/12113; A61B 17/12118; A61B 2017/1205; A61B 2017/12054; A61M 2025/0915; A61M 2025/09133
  See application file for complete search history.

(56) References Cited

U.S. PATENT DOCUMENTS

| | | | |
|---|---|---|---|
| 4,545,390 A | * | 10/1985 | Leary .............. A61M 25/09033 600/462 |
| 4,994,069 A | | 2/1991 | Ritchart et al. |

(Continued)

FOREIGN PATENT DOCUMENTS

| | | |
|---|---|---|
| DE | 10325130 | 9/2004 |
| WO | 9942038 | 8/1999 |

(Continued)

OTHER PUBLICATIONS

Response to office action dated Nov. 12, 2010 for application U.S. Appl. No. 12/122,636, response submitted Mar. 14, 2011 (13 pages).

(Continued)

*Primary Examiner* — Jonathan Miles
(74) *Attorney, Agent, or Firm* — Vista IP Law Group, LLP

(57) ABSTRACT

A delivery wire assembly for delivery of an occlusive device to a location in a patient's vasculature includes a delivery wire conduit having a proximal tubular portion connected to a distal coil portion, and a conduit lumen extending through the proximal tubular portion and the distal coil portion. The delivery wire assembly also includes a core wire disposed in the conduit lumen and having a distal end coupled to an occlusive device. The distal coil portion of the delivery wire assembly includes a plurality of zones and the plurality of zones decrease in stiffness distally along the length of the distal coil portion of the delivery wire assembly.

8 Claims, 5 Drawing Sheets

(52) U.S. Cl.
CPC ... *A61B17/12022* (2013.01); *A61B 17/12109* (2013.01); *A61B 17/12145* (2013.01); *A61B 90/39* (2016.02); *A61B 2017/12063* (2013.01); *A61B 2017/12068* (2013.01); *A61M 2025/0915* (2013.01); *A61M 2025/09133* (2013.01)

(56) References Cited

U.S. PATENT DOCUMENTS

| | | | |
|---|---|---|---|
| 5,122,136 | A | 6/1992 | Guglielmi et al. |
| 5,135,487 | A * | 8/1992 | Morrill et al. ...... A61M 25/104 604/103.09 |
| 5,226,911 | A | 7/1993 | Chee et al. |
| 5,304,194 | A | 4/1994 | Chee et al. |
| 5,382,259 | A | 1/1995 | Phelps et al. |
| 5,431,153 | A | 7/1995 | Lee |
| 5,549,624 | A | 8/1996 | Mirigian et al. |
| 5,582,619 | A | 12/1996 | Ken |
| 5,613,946 | A * | 3/1997 | McKeever .......... A61M 1/1072 604/96.01 |
| 5,690,666 | A | 11/1997 | Berenstein et al. |
| 5,725,534 | A * | 3/1998 | Rasmussen ...... A61B 17/12022 600/585 |
| 5,743,905 | A | 4/1998 | Eder et al. |
| 5,853,418 | A | 12/1998 | Ken et al. |
| 5,919,187 | A | 7/1999 | Guglielmi et al. |
| 5,984,929 | A | 11/1999 | Bashiri et al. |
| 6,059,779 | A | 5/2000 | Mills |
| 6,077,260 | A | 6/2000 | Wheelock et al. |
| 6,102,933 | A | 8/2000 | Lee et al. |
| 6,277,125 | B1 | 8/2001 | Barry et al. |
| 6,280,457 | B1 | 8/2001 | Wallace et al. |
| 6,409,721 | B1 | 6/2002 | Wheelock et al. |
| 6,468,266 | B1 | 10/2002 | Bashiri et al. |
| 6,537,293 | B1 | 3/2003 | Berryman et al. |
| 6,575,965 | B1 | 6/2003 | Benett et al. |
| 6,589,230 | B2 | 7/2003 | Gia et al. |
| 6,953,473 | B2 | 10/2005 | Porter |
| 7,198,613 | B2 | 4/2007 | Gandhi et al. |
| 7,381,198 | B2 * | 6/2008 | Noriega et al. ... A61M 25/0054 604/95.04 |
| 7,744,594 | B2 * | 6/2010 | Yamazaki et al. . A61B 18/1492 604/96.01 |
| 7,862,602 | B2 | 1/2011 | Licata et al. |
| 7,883,526 | B2 * | 2/2011 | Jones et al. ...... A61B 17/12022 606/191 |
| 7,921,848 | B2 | 4/2011 | Nikolchev et al. |
| 2001/0020174 | A1 * | 9/2001 | Koblish ............. A61B 18/1492 606/194 |
| 2002/0091380 | A1 | 7/2002 | Wheelock et al. |
| 2002/0151883 | A1 | 10/2002 | Guglielmi |
| 2003/0120300 | A1 | 6/2003 | Porter |
| 2003/0130689 | A1 | 7/2003 | Wallace et al. |
| 2003/0216685 | A1 * | 11/2003 | Porter ............. A61B 17/00491 604/82 |
| 2004/0002732 | A1 | 1/2004 | Teoh et al. |
| 2004/0002733 | A1 | 1/2004 | Teoh |
| 2004/0010243 | A1 | 1/2004 | Klint |
| 2004/0093009 | A1 * | 5/2004 | Denison et al. ........ A61F 2/013 606/200 |
| 2004/0127918 | A1 * | 7/2004 | Nikolchev et al. ................. A61B 17/12022 606/157 |
| 2006/0135986 | A1 | 6/2006 | Wallace et al. |
| 2006/0271097 | A1 | 11/2006 | Ramzipoor et al. |
| 2006/0282112 | A1 | 12/2006 | Griffin |
| 2007/0055302 | A1 | 3/2007 | Henry et al. |
| 2007/0123927 | A1 | 5/2007 | Farnan |
| 2008/0306504 | A1 | 12/2008 | Win et al. |
| 2009/0018653 | A1 | 1/2009 | Bashiri et al. |
| 2009/0062726 | A1 | 3/2009 | Ford et al. |
| 2009/0177261 | A1 | 7/2009 | Teoh et al. |
| 2009/0299275 | A1 | 12/2009 | Gandhi et al. |
| 2010/0010533 | A1 * | 1/2010 | Burke et al. ..... A61B 17/12022 606/200 |
| 2010/0094258 | A1 * | 4/2010 | Shimogami et al. ................. A61M 25/005 604/527 |
| 2010/0094395 | A1 | 4/2010 | Kellett |
| 2010/0114017 | A1 | 5/2010 | Lenker et al. |
| 2010/0234872 | A1 * | 9/2010 | Guo et al. ........ A61B 17/12022 606/191 |
| 2010/0268251 | A1 * | 10/2010 | Chen et al. ...... A61B 17/12022 606/139 |
| 2010/0268252 | A1 * | 10/2010 | Chen et al. ...... A61B 17/12022 606/139 |
| 2010/0324589 | A1 * | 12/2010 | Carpenter et al. ................. A61B 17/12022 606/200 |
| 2011/0106128 | A1 * | 5/2011 | Chen ................ A61B 17/12022 606/191 |
| 2011/0118772 | A1 * | 5/2011 | Chen et al. ...... A61B 17/12022 606/191 |
| 2011/0118776 | A1 * | 5/2011 | Chen et al. ...... A61B 17/12022 606/200 |
| 2011/0160835 | A1 | 6/2011 | Licata et al. |
| 2012/0209310 | A1 * | 8/2012 | Chen et al. ...... A61B 17/12022 606/195 |

FOREIGN PATENT DOCUMENTS

| | | |
|---|---|---|
| WO | 01/54761 | 8/2001 |
| WO | 03053281 | 7/2003 |
| WO | 2008/064206 | 5/2008 |
| WO | 2008/085606 | 7/2008 |
| WO | 2008/144587 | 11/2008 |

OTHER PUBLICATIONS

Office action for application U.S. Appl. No. 12/122,636 dated Jun. 7, 2011 (16 pages).
Response to office action for U.S. Appl. No. 12/122,636 dated Jun. 7, 2011, response submitted on Aug. 4, 2011 (10 pages).
Final office action for U.S. Appl. No. 12/122,636 dated Jan. 20, 2012 (9 pages).
Response to Final office action for U.S. Appl. No. 12/122,636 dated Jan. 20, 2012, response submitted on Feb. 28, 2012 (5 pages).
Office action for EP application No. 08755795.5 dated Jul. 15, 2011 (5 pages).
PCT International Search Report and Written Opinion for PCT/US2009/059797, Applicant Boston Scientific Scimed, Inc., Forms PCT/ISA/210, 220, and 237 dated Nov. 30, 2009 (14 pages).
PCT International Search Report and Written Opinion for PCT/US2008/064013, Applicant Boston Scientific Scimed, Inc., Forms PCT/ISA/210, 220, and 237 dated May 16, 2009 (16 pages).
PCT Invitation to Pay Additional Fees from the International Search Authority for PCT/US2008/064013, Applicant Boston Scientific Scimed, Inc., Form PCT/ISA/206 and Annex to Form PCT/ISA/206, dated Jan. 29, 2009 (5 pages).
PCT International Preliminary Report on Patentability for PCT/US2008/064013, Applicant Boston Scientific Scimed, Inc., dated Dec. 3, 2009 (8 pages).
Office action from related application JP 2012-503724 with translation provided by the Foreign Associate, dated Jan. 21, 2014 (9 pages).
Office action from the Chinese Patent Office for related application No. 201080015476.2, mailed May 24, 2013, translation provided by the foreign associate (7 pages).
PCT International Search Report and Written Opinion for PCT/US2010/056483, Applicant Boston Scientific Scimed, Inc., Forms PCT/ISA/210, 220, and 237, dated Apr. 8, 2011 (12 pages).
PCT International Search Report and Written Opinion for PCT/US2010/026831, Applicant Boston Scientific Scimed, Inc., Forms PCT/ISA/210, 220, and 237, dated Dec. 13, 2010 (16 pages).
PCT International Search Report for PCTUS2010/029700, Applicant Boston Scientific Scimed, Inc., Forms PCT/ISA 210 and 220, dated May 21, 2010 (12 pages).

(56) References Cited

OTHER PUBLICATIONS

Non final Office Action dated Nov. 12, 2010, for related U.S. Appl. No. 12/122,636, filed May 16, 2008, Inventor Russell Ford et al. (29 pages).

PCT Invitation to Pay Additional Fees from the International Search Authority for PCT/US2010/026831, Applicant Boston Scientific Scimed, Inc., Form PCT/ISA/206 and Annex to Form PCT/ISA/206, dated Jul. 23, 2010 (5 pages).

* cited by examiner

DELIVERY WIRE FOR OCCLUSIVE DEVICE DELIVERY SYSTEM

RELATED APPLICATION DATA

The present application is a continuation of pending U.S. patent application Ser. No. 12/752,914, filed Apr. 1, 2010, which claims the benefit under 35 U.S.C. §119 to U.S. Provisional application Ser. No. 61/166,888 filed Apr. 6, 2009. The foregoing applications are hereby incorporated by reference into the present application in their entirety.

FIELD OF THE INVENTION

The field of the invention generally relates to systems and delivery devices for implanting vaso-occlusive devices for establishing an embolus or vascular occlusion in a vessel of a human or veterinary patient.

BACKGROUND OF THE INVENTION

Vaso-occlusive devices or implants are used for a wide variety of reasons, including treatment of intra-vascular aneurysms. Commonly used vaso-occlusive devices include soft, helically wound coils formed by winding a platinum (or platinum alloy) wire strand about a "primary" mandrel. The relative stiffness of the coil will depend, among other things, on its composition, the diameter of the wire strand, the diameter of the primary mandrel, and the pitch of the resulting primary windings. The coil is then wrapped around a larger, "secondary" mandrel, and heat treated to impart a secondary shape. For example, U.S. Pat. No. 4,994,069, issued to Ritchart et al., describes a vaso-occlusive coil that assumes a linear, helical primary shape when stretched for placement through the lumen of a delivery catheter, and a folded, convoluted secondary shape when released from the delivery catheter and deposited in the vasculature.

In order to deliver the vaso-occlusive coils to a desired site in the vasculature, e.g., within an aneurismal sac, it is well-known to first position a small profile, delivery catheter or "micro-catheter" at the site using a steerable guidewire. Typically, the distal end of the micro-catheter is provided, either by the attending physician or by the manufacturer, with a selected pre-shaped bend, e.g., 45°, 90°, "J", "S", or other bending shape, depending on the particular anatomy of the patient, so that it will stay in a desired position for releasing one or more vaso-occlusive coil(s) into the aneurysm once the guidewire is withdrawn. A delivery or "pusher" wire is then passed through the micro-catheter, until a vaso-occlusive coil coupled to a distal end of the delivery wire is extended out of the distal end opening of the micro-catheter and into the aneurysm. The vaso-occlusive device is then released or "detached" from the end delivery wire, and the delivery wire is withdrawn back through the catheter. Depending on the particular needs of the patient, one or more additional occlusive devices may be pushed through the catheter and released at the same site.

One well-known way to release a vaso-occlusive coil from the end of the pusher wire is through the use of an electrolytically severable junction, which is a small exposed section or detachment zone located along a distal end portion of the pusher wire. The detachment zone is typically made of stainless steel and is located just proximal of the vaso-occlusive device. An electrolytically severable junction is susceptible to electrolysis and disintegrates when the pusher wire is electrically charged in the presence of an ionic solution, such as blood or other bodily fluids. Once the detachment zone exits out of the catheter distal end and is exposed in the vessel blood pool of the patient, a current applied through an electrical contact to the conductive pusher wire completes a circuit with a return electrode, and the detachment zone disintegrates due to electrolysis. Return electrodes include electrodes attached to the patient's skin, conductive needles inserted through the skin at a remote site, and electrodes located on the pusher wire but electrically insulated from the conductive path ending in the detachment zone.

One perceived problem with current vaso-occlusive coil delivery systems is that the detachment zone of the pusher wire bends as the vaso-occlusive coil is pushed through the micro-catheter. Orthogonal forces generated as a stiff pusher wire takes on the shapes of various bends in the micro-catheter may be sufficient to bend the detachment zone. This bending may adversely impact the placement of the embolic coil within the aneurysm and detachment of the embolic coil by electrolysis.

Another perceived problem is that pusher wires tend to have a stiff distal section that complicates accurate placement of the delivery system at the desired location, i.e., a stiff distal section of the pusher wire can cause a pre-shaped micro-catheter to kick back or recoil from the aneurysm upon coil deployment and release.

SUMMARY

In accordance with various embodiments, a delivery wire assembly for delivery of occlusive devices to locations in a patient's vasculature includes a delivery wire conduit having a proximal tubular portion connected to a distal coil portion, and a conduit lumen extending through the proximal tubular portion and the distal coil portion. The delivery wire assembly also includes a core wire disposed in the conduit lumen and having a distal end coupled to an occlusive device. The distal coil portion of the delivery wire assembly includes a plurality of coils formed from coil wire, including one or more respective proximal, middle and distal coils, which decrease in stiffness distally along the length of the distal coil portion of the delivery wire assembly. The stiffness of the middle coil may be, by way of non-limiting example, 86-95% of the stiffness of the proximal coil, and the stiffness of the distal coil (again, by way of non-limiting example) may be 80-85% of the stiffness of the proximal coil.

In some embodiments, the most proximal coil(s) may have a pitch of about 0%, the middle coil(s) have a pitch in the range of 5-9%, and the most distal coil(s) have a pitch in the range of 10-20%. In some embodiments, the coil wire of the proximal coil(s) has an outer diameter of about 0.00250 inches, the coil wire of the middle coil(s) has an outer diameter of about 0.00225 inches, and the coil wire of the most distal coil(s) has an outer diameter of about 0.00200 inches. In some embodiments, the coil wire of the proximal coil(s) has an ultimate tensile strength in the range of 300-350 ksi, the coil wire of the middle coil(s) has an ultimate tensile strength in the range of 250-299 ksi, and the coil wire of the most distal coil(s) has an ultimate tensile strength in the range of 200-249 ksi. In some embodiments, the coil wire of the proximal coil(s) has a higher modulus of elasticity than the coil wire of the middle coil(s), and the coil wire of the middle coil(s) has a higher modulus of elasticity than the coil wire of the distal coil(s). In some embodiments, the coil wire of the proximal coil(s) has a circular cross section, the coil wire of the middle coil(s) has an ellipsoid cross section, and the coil wire of the distal coil(s) has an ellipsoid cross section with a larger major axis than the ellipsoid cross section of the coil wire of the middle coil(s). In some embodiments, the coil wire is laminated, wherein the lamination covering the coil wire of the proximal coil(s) is thicker than the lamination covering the coil wire of the middle zone, and the lamination covering the coil wire of the middle coil(s) is thicker than the lamination covering the coil wire of the distal coil(s).

In another alternative embodiment, an occlusive device delivery system includes a delivery catheter having a proximal end, a distal end, and a catheter lumen extending between the proximal and distal ends. The occlusive device delivery system according to this further alternative embodiment also includes a delivery wire assembly having a delivery wire conduit having a proximal tubular portion connected to a distal coil portion, and a conduit lumen extending through the proximal tubular portion and the distal coil portion, and a core wire disposed in the conduit lumen and having a distal end coupled to an occlusive device via an electrolytically severable junction. The distal coil portion of the delivery wire assembly includes a plurality of coils that decrease in stiffness distally along the length of the distal coil portion of the delivery wire assembly. The occlusive device delivery system also includes a power supply electrically connected to the core wire.

BRIEF DESCRIPTION OF THE DRAWINGS

Referring now to the drawings in which like reference numbers represent corresponding parts throughout, and in which.

DETAILED DESCRIPTION OF THE ILLUSTRATED EMBODIMENTS

Figure 1:
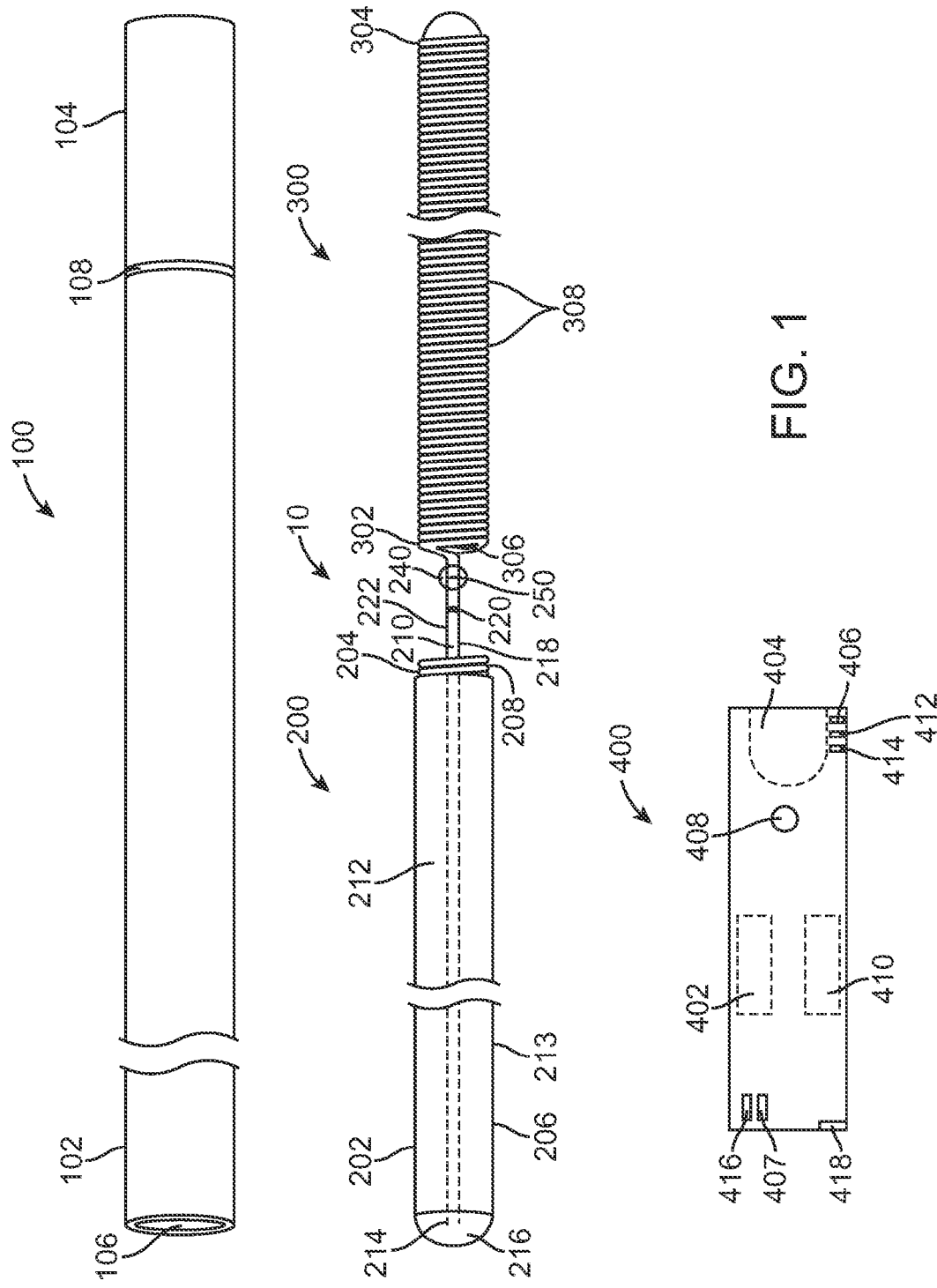
FIG. 1 illustrates an occlusive coil delivery system, according to one embodiment.

FIG. 1 illustrates an occlusive coil delivery system 10 according to one embodiment. The system 10 includes a number of subcomponents or sub-systems. These include a delivery catheter 100, a delivery wire assembly 200, an occlusive coil 300, and a power supply 400. The delivery catheter 100 includes a proximal end 102, a distal end 104, and a lumen 106 extending between the proximal and distal ends 102, 104. The lumen 106 of the delivery catheter 100 is sized to accommodate axial movement of the delivery wire assembly 200. Further, the lumen 106 is sized for the passage of a guidewire (not shown) which may optionally be used to properly guide the delivery catheter 100 to the appropriate delivery site.

The delivery catheter 100 may include a braided-shaft construction of stainless steel flat wire that is encapsulated or surrounded by a polymer coating. For example, HYDROLENE® is one exemplary polymer coating that may be used to cover the exterior portion of the delivery catheter 100. Of course, the system 10 is not limited to a particular construction or type of delivery catheter 100 and other constructions known to those skilled in the art may be used for the delivery catheter 100.

The inner lumen 106 is advantageously coated with a lubricious coating such as PTFE to reduce frictional forces between the delivery catheter 100 and the device that is being moved axially within the lumen 106. The delivery catheter 100 may include one or more optional marker bands 108 formed from a radiopaque material that can be used to identify the location of the delivery catheter 100 within the patient's vasculature system using imaging technology (e.g., fluoroscope imaging). The length of the delivery catheter 100 may vary depending on the particular application but generally is around 150 cm in length. Of course, other lengths of the delivery catheter 100 may be used with the system 10 described herein.

The delivery catheter 100 may include a distal end 104 that is straight as illustrated in FIG. 1. Alternatively, the distal end 104 may be pre-shaped into a specific geometry or orientation. For example, the distal end 104 may be shaped into a "C" shape, an "S" shape, a "J" shape, a 45° bend, a 90° bend. The size of the lumen 106 may vary depending on the size of the delivery wire assembly 200 and occlusive coil 300 but generally the diameter lumen 106 of the delivery catheter 100 (I.D. of delivery catheter 100) is less than about 0.02 inches. The delivery catheter 100 is known to those skilled in the art as a microcatheter. While not illustrated in FIG. 1, the delivery catheter 100 may be utilized with a separate guide catheter (not shown) that aids in guiding the delivery catheter 100 to the appropriate location within the patient's vasculature.

Still referring to FIG. 1, the system 10 includes a delivery wire assembly 200 that is configured for axial movement within the lumen 106 of the delivery catheter 100. The delivery wire assembly 200 generally includes a proximal end 202 and a distal end 204. The delivery wire assembly 200 includes a delivery wire conduit 213, which has a proximal tubular portion 206 and a distal coil portion 208. The proximal tubular portion 206 may be formed from, for example, stainless steel hypotube. The distal coil portion 208 may be formed from, for example, stainless steel wire. The distal coil portion 208 may be bonded to the proximal tubular portion 206 in an end-to-end arrangement.

The delivery wire assembly 200 further includes a core wire 210 that extends from the proximal end 202 of the delivery wire assembly 200 to a location that is distal with respect to the distal end 204 of the delivery wire assembly 200. The core wire 210 is disposed within a lumen 212 that extends within an interior portion of the delivery wire conduit 213. The core wire 210 is formed from an electrically conductive material such as stainless steel wire. The proximal end 214 of the core wire 210 (shown in phantom) is electrically coupled to an electrical contact 216 located at the proximal end 202 of the delivery wire assembly 200. The electrical contact 216 may be formed from a metallic solder (e.g., gold) that is configured to interface with a corresponding electrical contact (not shown) in the power supply 400.

A portion of the core wire 210 is advantageously coated with an insulative coating 218. The insulative coating 218 may include polyimide. The entire length of the core wire 210 is coated with an insulative coating 218 except for the proximal end 214 of the core wire 210 that is in contact with electrical contact 216 and a small region 220 located in a portion of the core wire 210 that extends distally with respect to the distal end 204 of the of the delivery wire assembly 200. This latter "bare" portion of the core wire 210 forms the electrolytic detachment zone 220 which dissolves upon application of electrical current from the power supply 400.

In an alternative embodiment, instead of an electrolytic detachment zone 220, the sacrificial region may be configured to break or dissolve in response to thermal energy. For example, the detachment zone 220 may be formed from a polymeric link (e.g., fiber(s)) that melts or dissolves in response to externally applied thermal energy or heat. The polymeric link may be formed from a thermoplastic material (e.g., polyethylene) that has a high tensile strength and appropriate melting temperature. The thermally responsive sacrificial region may be responsive to an electrical resistance heater coil that is configured to apply heat to the detachment zone 220. Such heater coils operate by generating heat in response to an applied electrical current. Alternatively, electromagnetic or RF energy may be used to break or dissolve the sacrificial region. U.S. Pat. No. 7,198, 613, which is incorporated herein by reference, discloses additional details regarding various thermally-actuated detachment modalities.

Still referring to FIG. 1, the occlusive coil 300 includes a proximal end 302, a distal end 304 and a lumen 306 extending there between. The occlusive coil 300 is generally made from a biocompatible metal such as platinum or a platinum alloy (e.g., platinum-tungsten alloy). The occlusive coil 300 generally includes a straight configuration (as illustrated in FIG. 1) when the occlusive coil 300 is loaded within the delivery catheter 100. Upon release, the occlusive coil 300 generally takes a secondary shape which may include two-dimensional or three-dimensional configurations such as that illustrated in FIG. 4. Of course, the system 10 described herein may be used with occlusive coils 300 having a variety of configurations and is not limited to particular occlusive coils 300 having a certain size or configuration.

The occlusive coil 300 includes a plurality of coil windings 308. The coil windings 308 are generally helical about a central axis disposed along the lumen 306 of the occlusive coil 300. The occlusive coil 300 may have a closed pitch configuration as illustrated in FIG. 1.

The distal end 222 of the core wire 210 is connected to the proximal end 302 of the occlusive coil 300 at a junction 250. Various techniques and devices can be used to connect the core wire 210 to the occlusive coil 300, including laser melting, and laser tack, spot, and continuous welding. It is preferable to apply an adhesive 240 to cover the junction 250 formed between the distal end 222 of the core wire 210 and the proximal end 302 of the occlusion coil 300. The adhesive 240 may include an epoxy material which is cured or hardened through the application of heat or UV radiation. For example, the adhesive 240 may include a thermally cured, two-part epoxy such as EPO-TEK® 353ND-4 available from Epoxy Technology, Inc., 14 Fortune Drive, Billerica, Mass. The adhesive 240 encapsulates the junction 250 and increases its mechanical stability.

Still referring to FIG. 1, the system 10 includes a power supply 400 for supplying direct current to the core wire 210 which contains the electrolytic detachment zone 220. In the presence of an electrically conductive fluid (which may include a physiological fluid such as blood or a flushing solution such as saline), when the power supply 400 is activated, electrical current flows in a circuit including the electrical contact 216, the core wire 210, the electrolytic detachment zone 220, and a return electrode (not shown). After several seconds (generally less than about 10 seconds), the sacrificial electrolytic detachment zone 220 dissolves and the occlusive coil 300 separates form the core wire 210.

The power supply 400 will include an onboard energy source such as batteries (e.g., a pair of AAA batteries) along with drive circuitry 402. The drive circuitry 402 may include one or more microcontrollers or processors configured to output a driving current. The power supply 400 illustrated in FIG. 1 includes a receptacle 404 that is configured to receive and mate with the proximal end 202 of the delivery wire assembly 200. Upon insertion of the proximal end 202 into the receptacle 404, the electrical contact 216 disposed on the delivery wire assembly 200 electrically couple with corresponding contacts (not shown) located in the power supply 400.

A visual indicator 406 (e.g., LED light) may indicate when the proximal end 202 of delivery wire assembly 200 has been properly inserted into the power supply 400. Another visual indicator 407 may activate if the batteries need to be replaced. The power supply 400 typically includes an activation trigger or button 408 that is depressed by the user to apply the electrical current to the sacrificial electrolytic detachment zone 220. Typically, once the activation trigger 408 has been activated, the driver circuitry 402 automatically supplies current until detachment occurs. The drive circuitry 402 typically operates by applying a substantially constant current (e.g., around 1.5 mA).

The power supply 400 may include optional detection circuitry 410 that is configured to detect when the occlusive coil 300 has detached from the core wire 210. The detection circuitry 410 may identify detachment based upon a measured impedance value. A visual indicator 412 may indicate when the power supply 400 is being supplied to the current to the sacrificial electrolytic detachment zone 220. Another visual indicator 414 may indicate when the occlusive coil 300 has detached from the core wire 210. As an alternative to the visual indicator 414, an audible signal (e.g., beep) or even tactile signal (e.g., vibration or buzzer) may be triggered upon detachment. The detection circuitry 410 may be configured to disable the drive circuitry 402 upon sensing detachment of the occlusive coil 300.

The power supply 400 may also contain another visual indicator 416 that indicates to the operator when non-bipolar delivery wire assembly is inserted into the power supply 400. As explained in the background above, non-bipolar delivery wire assemblies use a separate return electrode that typically is in the form of a needle that was inserted into the groin area of the patient. The power supply 400 is configured to detect when a non-bipolar delivery wire assembly has been inserted. Under such situations, the visual indicator 416 (e.g., LED) is turned on and the user is advised to insert the separate return electrode (not shown in FIG. 1) into a port 418 located on the power supply 400.

Figure 2:
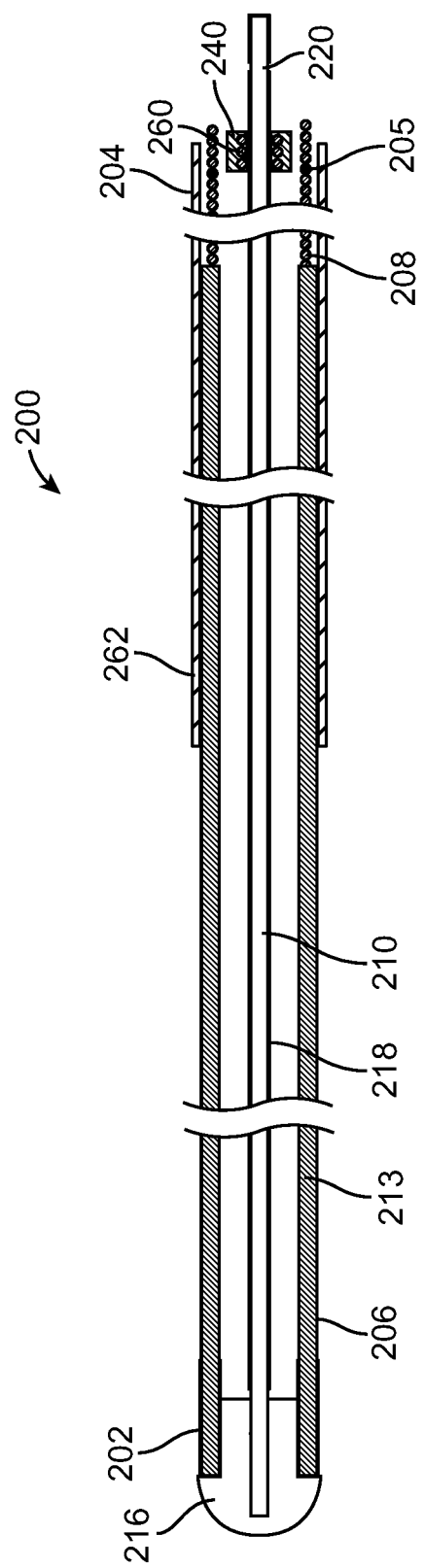
FIG. 2 is a longitudinal cross-sectional view of a delivery wire assembly, according to one embodiment.

FIG. 2 illustrates a cross-sectional view of the delivery wire assembly 200 according to one embodiment. Similar elements of this embodiment are identified with the same reference numbers as discussed above with respect to FIG. 1. The delivery wire assembly 200 includes a proximal end 202 and a distal end 204 and measures between around 184 cm to around 186 cm in length. The delivery wire assembly 200 includes a delivery wire conduit 213 with a proximal tubular portion 206 and a distal coil portion 208. The proximal tubular portion 206 may be formed from stainless steel hypotube having an outer diameter (OD) of 0.01325 inches and inner diameter (ID) of 0.0075 inches. The length of the hypotube section may be between around 140 cm to around 150 cm, although other lengths may also be used.

As seen in FIG. 2, a distal coil portion 208 is bonded in end-to-end fashion to the distal face of the proximal tubular portion 206. The bonding may be accomplished using a weld or other bond. The distal coil portion 208 may have a length of around 39 cm to around 41 cm in length. The distal coil portion 208 may comprise a coil of 0.0025 inches×0.006 inches. The first dimension generally refers to the OD of the coil wire that forms the coil. The latter dimension generally refers to the internal mandrel used to wind the coil wire around to form the plurality of coil winds and is the nominal ID of the coil.

The distal coil portion 206 is divided into three coil "zones", a proximal zone 224, a middle zone 226, and a distal zone 228, each zone made of one or more coils, wherein the coils of each zone differ from each other, including proximal coils 234, middle coils 236, and distal coils 238. The three types of coils are, in turn, made up of three types of coil wire, proximal coil wire 244, middle coil wire 246, and distal coil wire 248. These zones decrease in stiffness distally along the length of the distal coil portion 206 of the delivery wire assembly 200. In other words, the proximal zone 224 is stiffer than the middle zone 226, and the middle zone 226 is stiffer than the distal zone 228. In one embodiment, the stiffness of the middle zone is about 86-95% of the stiffness of the proximal zone, and the stiffness of the distal zone is about 80-85% of the stiffness of the proximal zone. This gradual decrease in stiffness along the length of the distal coil portion 206 minimizes bending, by releasing stress, and maximizes pushability and trackability. This smooth stiffness transition also reduces kick back on the delivery catheter 100 during deployment and detachment of the occlusive coil 300.

Figure 3A:
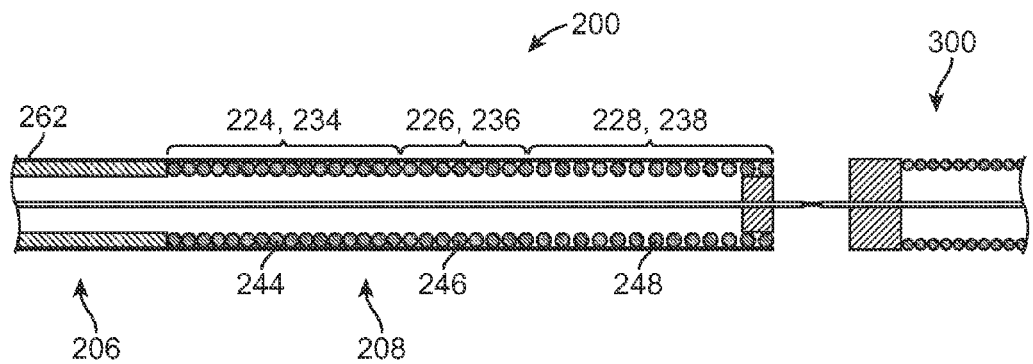
FIG. 3A to 3F are detailed longitudinal cross-sectional views of delivery wire assemblies, according to various embodiments.

In order to achieve the decrease in stiffness, various embodiments of the invention include coils and/or coil wires that vary between zones. In one embodiment, as shown in FIG. 3A, the pitch of the coils increases distally. Proximal coils 234 have a pitch of about 0%, middle coils 236 have a pitch in the range of 5-9%, and distal coils 238 have a pitch in the range of 10-20%.

Figure 3B:
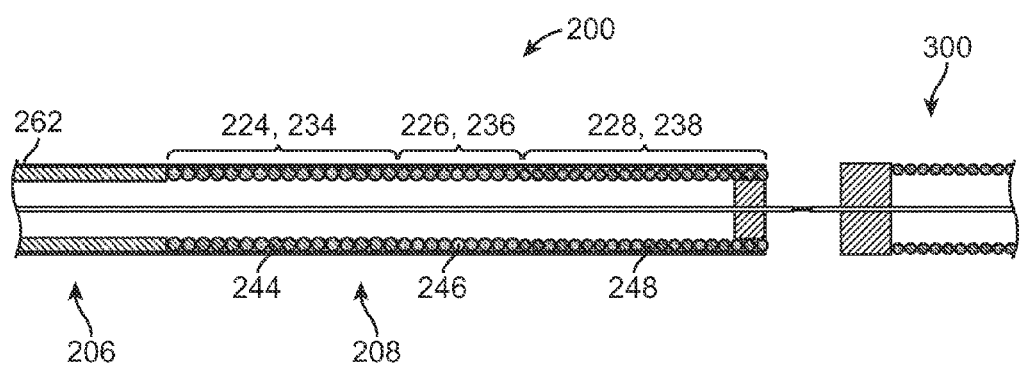

In another embodiment, as shown in FIG. 3B, the OD of the coil wire decreases distally. Proximal coil wire 244 has an OD of about 0.00250 inches, middle coil wire 246 has an OD of about 0.00225 inches, and distal coil wire 248 has an OD of about 0.00200 inches.

Figure 3C:
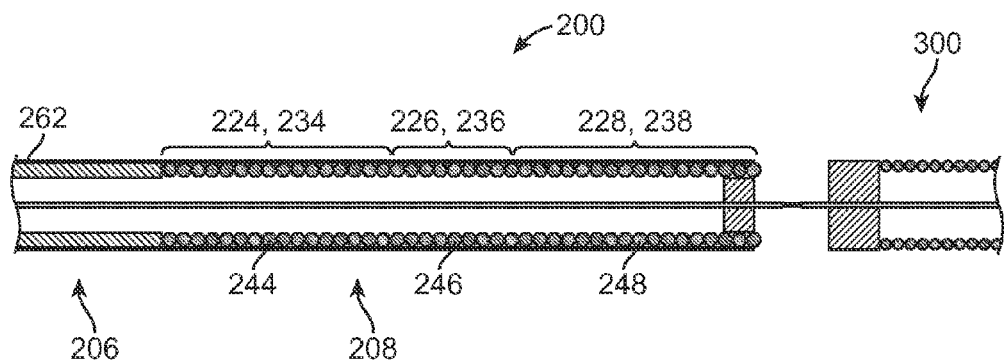

In yet another embodiment, as shown in FIG. 3C, the tensile strength of the coil wire decreases distally. Proximal coil wire 244 has tensile strength of about 300-350 ksi, middle coil wire 246 has tensile strength of about 250-299 ksi, and distal coil wire 248 has tensile strength of about 200-249 ksi.

Figure 3D:
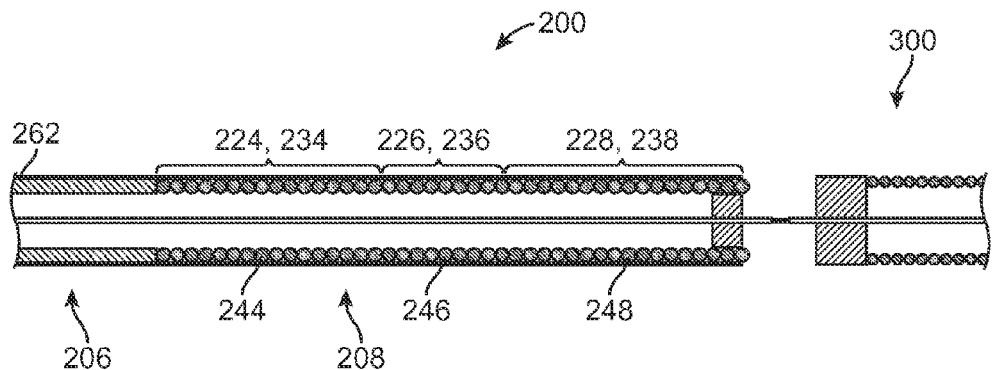

In still another embodiment, as shown in FIG. 3D, the modulus of elasticity of the coil wire decreases distally. Proximal coil wire 244 has a higher modulus of elasticity than that of middle coil wire 246, which has a higher modulus of elasticity than that of distal coil wire 248.

Figure 3E:
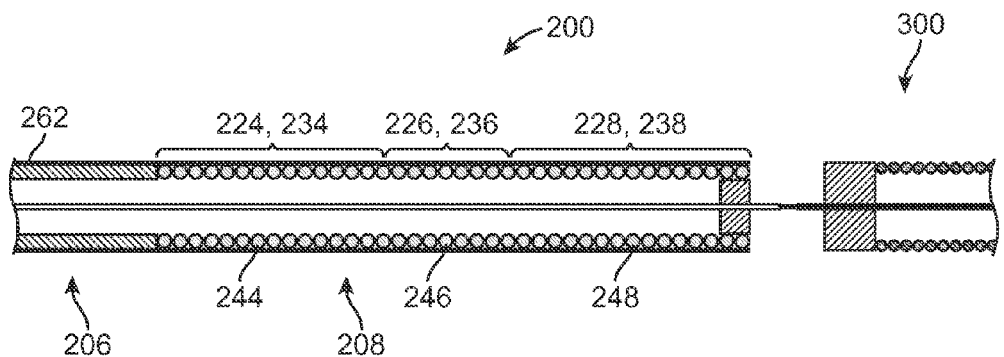

In another embodiment, as shown in FIG. 3E, the cross section of the coil wire changes from circular to more ellipsoid. Proximal coil wire 244 has a circular cross section, middle coil wire 246 has an ellipsoid cross section, and distal coil wire 248 has an even more ellipsoid cross section, i.e., an ellipse having a larger major axis.

Figure 3F:
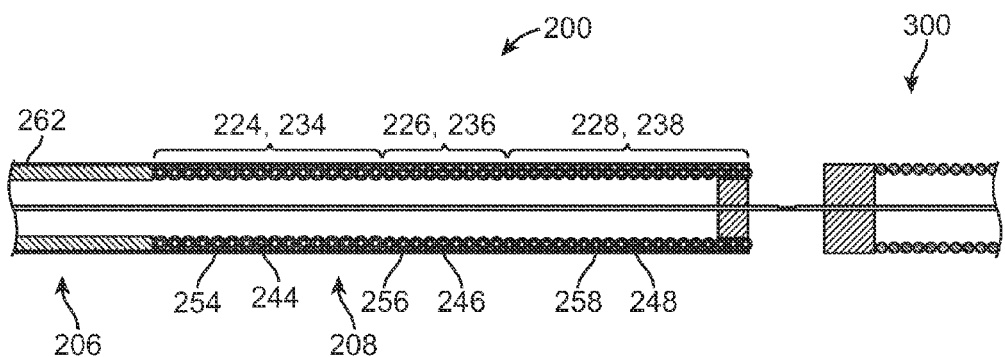

In yet another embodiment, as shown in FIG. 3F, coil wire is laminated and the lamination becomes thinner distally. Proximal coil wire lamination 254 is thicker than middle coil lamination 256, which is, in turn, thicker than distal coil lamination 258.

Although three zones are described for this embodiment, this invention is not limited to delivery wire assemblies with distal coil portions having three zones. In alternative embodiments, the changes in the distal coil portion are continuous, instead of discrete.

Referring to FIG. 2, one or more marker coils 205 of the distal coil portion 208 may be formed from a radiopaque material (illustrated as solid marker coils 205 in distal coil portion 208). For example, the distal coil portion 208 may include a segment of stainless steel coil (e.g., 3 cm in length), followed by a segment of platinum coil (which is radiopaque and also 3 mm in length), followed by a segment of stainless steel coil (e.g., 37 cm in length), and so on and so forth.

The core wire 210 terminates at electrical contact 216 at one end and extends distally with respect to the distal coil portion 208 of the delivery wire conduit 213. The core wire 210 is coated with an insulative coating 218 such as polyimide except at the electrolytic detachment zone 220 and the proximal segment coupled to the electrical contact 216. The electrolytic detachment zone 220 is located several millimeters (e.g., about 0.02 mm to about 0.2 mm) distally with respect to the distal end of the distal coil portion 208. The core wire 210 may have an OD of around 0.0175 inches. A centering coil 260 is affixed to the core wire 210 at a location within the distal coil portion 208. The centering coil 260 ensures that the core wire 210 is properly oriented within the delivery wire assembly 200. The centering coil 260 may be bonded directly to the core wire 210 using an adhesive 240 such as that described herein. To this end, an adhesive 240 is applied to secure the core wire 210 and centering coil 260 to the distal coil portion 208. The adhesive 240 may include EPO-TEK® 353ND-4 described in more detail above.

Still referring to FIG. 2, an outer sleeve 262 or jacket surrounds a portion of the proximal tubular portion 206 and a portion of the distal coil portion 208 of the delivery wire conduit 213. The outer sleeve 262 covers the interface or joint formed between the proximal tubular portion 206 and the distal coil portion 208. The outer sleeve 262 may have a length of around 50 cm to around 54 cm. The outer sleeve 262 may be formed from a polyether block amide plastic material (e.g., PEBAX 7233 lamination). The outer sleeve 262 may include a lamination of PEBAX and HYDROLENE®. The OD of the outer sleeve 262 may be less than 0.02 inches and advantageously less than 0.015 inches.

Figure 4:
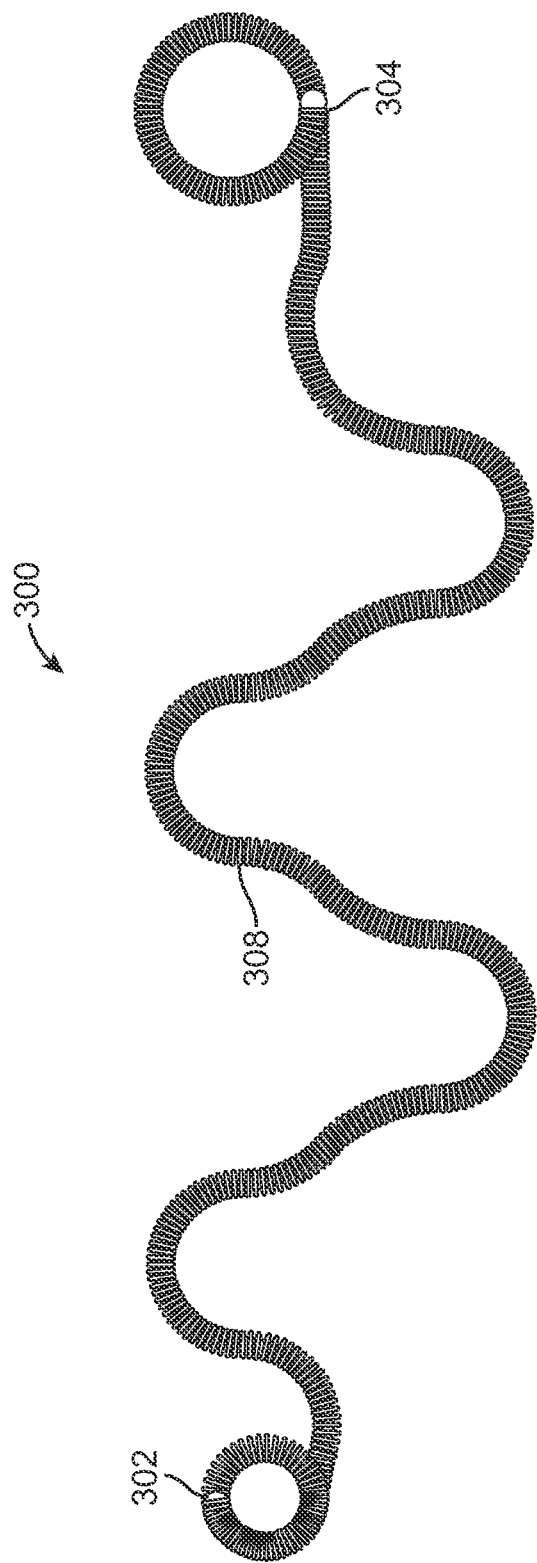
FIG. 4 illustrates an occlusive coil in a natural state mode, illustrating one exemplary secondary configuration.

FIG. 4 illustrates one exemplary configuration of an occlusive coil 300 in a natural state. In the natural state, the occlusive coil 300 transforms from the straight configuration illustrated in, for instance, FIG. 1 into a secondary shape. The secondary shaped may include both two and three dimensional shapes of a wide variety. FIG. 4 is just one example of a secondary shape of an occlusive coil 300 and other shapes and configurations are contemplated to fall within the scope of the invention. Also, the occlusive coil 300 may incorporate synthetic fibers over all or a portion of the occlusive coil 300 as is known in the art. These fibers may be attached directly to coil windings 308 or the fibers may be integrated into the occlusive coil 300 using a weave or braided configuration.

The electrical contact 216 may be manufactured by inserting a core wire 210 into the lumen 212 of the delivery wire conduit 213. Then a metallic solder can be applied to the proximal end 202 of the delivery wire assembly 200, forming the electrical contact 216. After the metallic solder is allowed to cure, clippers or the like may be used to trim the excess material. While various embodiments of the present invention have been shown and described, they are presented for purposes of illustration, and not limitation. Various modifications may be made to the illustrated and described embodiments without departing from the scope of the present invention, which is to be limited and defined only by the following claims and their equivalents.

What is claimed is:

1. A delivery wire assembly for delivery of an occlusive device to a vascular implantation location, comprising:
   a delivery wire conduit having a proximal tubular portion connected to a distal coil portion, and a conduit lumen extending through the respective proximal tubular portion and distal coil portion;
   a core wire extending into in the conduit lumen, the core wire being permanently fixed to the delivery wire conduit so that the core wire and the delivery wire conduit are not longitudinally movable relative to each other; and
   an occlusive device coupled to a distal end of the core wire,
   wherein the distal coil portion comprises a proximal zone including one or more proximal zone windings formed from a proximal zone laminated coil wire having a proximal zone lamination thickness, and a distal zone including one or more distal zone windings formed from a distal zone laminated coil wire having a distal zone lamination thickness less than the proximal zone lamination thickness.

2. The delivery wire assembly of claim 1, the proximal zone having a proximal zone stiffness, and the distal zone having a distal zone stiffness that is less than the proximal zone stiffness.

3. The delivery wire assembly of claim 1, wherein the distal coil portion further comprises a middle zone located between the respective proximal and distal zones, the middle zone including one or more middle zone windings formed from a middle zone laminated coil wire having a middle zone lamination thickness, wherein the middle zone lamination thickness is less than the proximal zone lamination thickness and greater than the distal zone lamination thickness.

4. The delivery wire assembly of claim 3, the proximal zone having a proximal zone stiffness, the middle zone having a middle zone stiffness that is less than the proximal zone stiffness, and the distal zone having a distal zone stiffness that is less than the middle zone stiffness.

5. An occlusive device delivery system, comprising:
   a delivery catheter having a proximal end, a distal end, and a catheter lumen extending between the proximal and distal ends;
   a delivery wire assembly, comprising
      a delivery wire conduit having a proximal tubular portion connected to a distal coil portion, and a conduit lumen extending through the respective proximal tubular portion and distal coil portion,
      a core wire extending into in the conduit lumen, the core wire being permanently fixed to the delivery wire conduit so that the core wire and the delivery wire conduit are not longitudinally movable relative to each other, and
      an occlusive device coupled to a distal end of the core wire,
      wherein the distal coil portion comprises a proximal zone including one or more proximal zone windings formed from a proximal zone laminated coil wire having a proximal zone lamination thickness, and a distal zone including one or more distal zone windings formed from a distal zone laminated coil wire having a distal zone lamination thickness less than the proximal zone lamination thickness; and
   a power supply electrically connected to the core wire.

6. The occlusive device delivery system of claim 5, the proximal zone of the distal coil portion having a proximal zone stiffness, and the distal zone of the distal coil portion having a distal zone stiffness that is less than the proximal zone stiffness.

7. The occlusive device delivery system of claim 5, the distal coil portion further comprising a middle zone located between the respective proximal and distal zones, the middle zone including one or more middle zone windings formed from a middle zone laminated coil wire having a middle zone lamination thickness, wherein the middle zone lamination thickness is less than the proximal zone lamination thickness and greater than the distal zone lamination thickness.

8. The delivery wire assembly of claim 7, the proximal zone having a proximal zone stiffness, the middle zone having a middle zone stiffness that is less than the proximal zone stiffness, and the distal zone having a distal zone stiffness that is less than the middle zone stiffness.

* * * * *